(12) United States Patent
San et al.

(10) Patent No.: US 8,906,667 B2
(45) Date of Patent: Dec. 9, 2014

(54) INCREASING NADPH-DEPENDENT PRODUCTS

(75) Inventors: Ka-Yiu San, Houston, TX (US); George Bennett, Houston, TX (US); Henry Lin, Houston, TX (US); Irene Martinez, Houston, TX (US); Jiangfeng Zhu, Houston, TX (US)

(73) Assignee: William Marsh Rice University, Houston, TX (US)

( * ) Notice: Subject to any disclaimer, the term of this patent is extended or adjusted under 35 U.S.C. 154(b) by 1241 days.

(21) Appl. No.: 12/439,497

(22) PCT Filed: Aug. 29, 2007

(86) PCT No.: PCT/US2007/077163
§ 371 (c)(1),
(2), (4) Date: Feb. 27, 2009

(87) PCT Pub. No.: WO2008/028002
PCT Pub. Date: Mar. 6, 2008

(65) Prior Publication Data
US 2010/0009418 A1 Jan. 14, 2010

Related U.S. Application Data

(60) Provisional application No. 60/823,829, filed on Aug. 29, 2006.

(51) Int. Cl.
| | | |
|---|---|---|
| *C12N 1/20* | (2006.01) |
| *C12N 15/00* | (2006.01) |
| *C12N 9/04* | (2006.01) |
| *C12N 9/02* | (2006.01) |
| *C12N 9/14* | (2006.01) |
| *C07H 21/04* | (2006.01) |
| *C07K 14/315* | (2006.01) |
| *C12N 15/70* | (2006.01) |
| *A61K 38/48* | (2006.01) |
| *C07K 14/30* | (2006.01) |
| *C07K 14/33* | (2006.01) |
| *C07K 14/395* | (2006.01) |
| *C12P 17/06* | (2006.01) |
| *C12P 23/00* | (2006.01) |

(52) U.S. Cl.
CPC .............. *C07K 14/315* (2013.01); *C12N 15/70* (2013.01); *A61K 38/484* (2013.01); *C07K 14/30* (2013.01); *C07K 14/33* (2013.01); *C07K 14/395* (2013.01); *C12N 9/0006* (2013.01); *C12P 17/06* (2013.01); *C12P 23/00* (2013.01)
USPC ...... 435/252.33; 435/190; 435/189; 435/195; 435/320.1; 435/440; 536/23.2

(58) Field of Classification Search
CPC ........ C12N 9/006; C12N 15/70; C12P 17/06; C12P 23/00
See application file for complete search history.

(56) References Cited

U.S. PATENT DOCUMENTS

| | | | |
|---|---|---|---|
| 7,326,557 B2 * | 2/2008 | San et al. ................ 435/252.3 |
| 7,566,553 B2 * | 7/2009 | Park et al. .................. 435/115 |
| 2005/0196866 A1 * | 9/2005 | San et al. .................... 435/488 |

FOREIGN PATENT DOCUMENTS

WO    WO2006/071086    7/2006

OTHER PUBLICATIONS

Valverde et al. Functional complementation of an *Escherichia coli* gap mutant supports an amphibolic role for NAD(P)-dependent glyceraldehyde-3-phosphate dehydrogenase of *Synechocystis* sp. strain PCC 6803. J Bacteriol. Jul. 1997;179(14):4513-22.*
Holland et al. The primary structure of a glyceraldehyde-3-phosphate dehydrogenase gene from *Saccharomyces cerevisiae*. J Biol Chem. Oct. 10, 1979;254(19):9839-45.*
Martinez et al. Replacing *Escherichia coli* NAD-dependent glyceraldehyde 3-phosphate dehydrogenase (GAPDH) with a NADP-dependent enzyme from *Clostridium acetobutylicum* facilitates NADPH dependent pathways. Metab Eng. Nov. 2008;10(6):352-9. Epub Sep. 23, 2008.*
Iddard et al. Widespread occurrence of non-phosphorylating glyceraldehyde-3-phosphate dehydrogenase among gram-positive bacteria. Int Microbiol. Dec. 2005;8(4):251-8.*
Schreiber et al. The glyceraldehyde-3-phosphate dehydrogenase of *Clostridium acetobutylicum*: isolation and purification of the enzyme, and sequencing and localization of the gap gene within a cluster of other glycolytic genes. Microbiology. Aug. 1999;145 ( Pt 8):1839-47.*
O52631. TREMBLREL Database. Jun. 1, 1998.*
Valverde et al. Engineering a central metabolic pathway: glycolysis with no net phosphorylation in an *Escherichia coli* gap mutant complemented with a plant GapN gene. FEBS Lett. Apr. 23, 1999;449(2-3):153-8.*
Alper et al. Identifying gene targets for the metabolic engineering of lycopene biosynthesis in *Escherichia coli*. Metab Eng. May 2005;7(3):155-64.*
PCT/US07/77163 Search Report, Dec. 12, 2007, Rice University.
Arkblad, et al., "The cDNA sequence of proton-pumping nicotinamide nucleotide transhydrogenase from man and mouse," Biochim Biophys Acta. 1273:203-5 (1996).
Arp, et al., "Molecular and cellular fundamentals of aerobic cometabolism of trichloroethylene," Biodegradation. 12:81-103 (2001).

(Continued)

*Primary Examiner* — Yong Pak
(74) *Attorney, Agent, or Firm* — Boulware & Valoir

(57) ABSTRACT

A method of increasing cellular NADPH levels by expressing one or more genes that encode an enzyme that causes the production of NADPH. The system is combined with other enzymes that require NADPH, thus improving the overall yield of the desired product.

5 Claims, 5 Drawing Sheets

(56) References Cited

OTHER PUBLICATIONS

Brzostowicz, et al., "Identification of two gene clusters involved in cyclohexanone oxidation in *Brevibacterium epidermidis* strain HCU," Appl. Microbiol. Biotechnol. 58:781-9 (2002).

Brzostowicz, et al., "mRNA differential display in a microbial enrichment culture: simultaneous identification of three cyclohexanone monooxygenases from three species," Appl. Environ. Microbiol. 69(1):334-42 (2003).

Choi, et al., "A novel flavin-containing monooxygenase from *Methylophaga* sp strain SK1 and its indigo synthesis in *Escherichia coli*," Biochem. Biophys. Res. Commun. 306(4):930-6 (2003).

Christensen et al., "Isotopomer analysis using GC-MS," Metab. Eng. 1:282-90 (1999).

Clarke, et al., "Nucleotide sequence of the pntA and pntB genes encoding the pyridine nucleotide transhydrogenase of *Escherichia coli*," Eur. J. Biochem. 158:647-53 (1986).

Datsenko et al., "One-step inactivation of chromosomal genes in *Escherichia coli* K-12 using PCR products," Proc. Natl. Acad. Sci. U. S. A. 97:6640-5 (2000).

Fillinger, et al. "Two glyceraldehyde-3-phosphate dehydrogenases with opposite physiological roles in a nonphotosynthetic bacterium," J. Biol. Chem. 275:14031-7 (2000).

Fishman, et al., "Controlling the regiospecific oxidation of aromatics via active site engineering of toluene para-monooxygenase of *Ralstonia pickettii* PKO1," J. Biol. Chem. 280:506-14 (2005).

Fishman, et al., "Protein engineering of toluene 4-monooxygenase of *Pseudomonas mendocina* KR1 for synthesizing 4-nitrocatechol from nitrobenzene," Biotechnol Bioeng. 87:779-90 (2004).

Fitzpatrick, "Mechanism of aromatic amino acid hydroxylation," Biochemistry. 42:14083-91 (2003).

Fraaije, et al., "Discovery of a thermostable Baeyer-Villiger monooxygenase by genome mining," Appl. Microbiol. Biotechnol. 66(4):393-400 (2005).

Iwaki, et al., "Cloning and characterization of a gene cluster involved in cyclopentanol metabolism in *Comamonas* sp. strain NCIMB 9872 and biotransformations effected by *Escherichia coli*-expressed cyclopentanone 1,2-monooxygenase," Appl. Environ. Microbiol. 68(11):5671-84 (2002).

Johanson, et al., "Strain engineering for stereoselective bioreduction of dicarbonyl compounds by yeast reductases," FEMS Yeast Res. 5:513-25 (2005).

Kamerbeek, et al., "Substrate specificity and enantioselectivity of 4-hydroxyacetophenone monooxygenase," Appl. Environ. Microbiol. 69:419-26 (2003).

Kamerbeek, et al., "Identifying determinants of NADPH specificity in Baeyer-Villiger monooxygenases," Eur. J. Biochem. 271:2107-16 (2004).

Kataoka, et al., "Novel bioreduction system for the production of chiral alcohols," Appl. Microbiol. Biotechnol. 62:437-445 (2003).

Kizaki, et al., "Synthesis of optically pure ethyl (S)-4-chloro-3-hydroxybutanoate by *Escherichia coli* transformant cells coexpressing the carbonyl reductase and glucose dehydrogenase genes," Appl. Microbiol. Biotechnol. 55(5):590-5 (2001).

Kyte, et al., "Assessing the substrate selectivities and enantioselectivities of eight novel Baeyer-Villiger monooxygenases toward alkyl-substituted cyclohexanones," J. Org. Chem. 69(1):12-7 (2004).

Langenbach, et al., "Functional expression of the PHA synthase gene phaC1 from *Pseudomonas aeruginosa* in *Escherichia coli* results in poly(3-hydroxyalkanoate) synthesis." FEMS Micorbiol. Lett. 150:303-9 (1997).

Leahy, et al., "Evolution of the soluble diiron monooxygenases," FEMS Microbiol. Rev. 27:449-79 (2003).

Liu, et al., "Asymmetric reduction of ethyl 4-chloro-3-oxobutanoate to ethyl (R)-4-chloro-3-hydroxybutanoate with two co-existing, recombinant *Escherichia coli* strains," Biotechnol. Lett. 27(2):119-25 (2005).

Maicas, S., et al., "NAD(P)H regeneration is the key for heterolactic fermentation of hexoses in *Oenococcus oeni*," Microbiology 148:325-32 (2002).

Malito, et al., "Crystal structure of a Baeyer-Villiger monooxygenase," Proc. Natl. Acad. Sci. U S A. 101(36):13157-62 (2004).

McClay, et al., "Mutations of toluene-4-monooxygenase that alter regiospecificity of indole oxidation and lead to production of novel indigoid pigments," Appl. Environ. Microbiol. 71:5476-83 (2005).

Mihovilovic, et al., "Asymmetric Baeyer-Villiger oxidations of 4-mono-and 4,4-disubstituted cyclohexanones by whole cells of engineered *Escherichia coli*." J. Org. Chem. 66(3):733-8 (2001).

Mihovilovic, et al., "First enantiodivergent Baeyer-Villiger oxidation by recombinant whole-cells expressing two monooxygenases from *Brevibacterium*," Bioorg. Med. Chem. Lett. 13(8):1479-82 (2003).

Qi, et al., "Synthesis of poly(3-hydroxyalkanoates) in *Escherichia coli* expressing the PHA synthase gene phaC2 from *Pseudomonas aeruginosa*: comparison of PhaC1 and PhaC2," FEMS Microbiol. Lett. 157:155-62 (1997).

Qi, et al., "Metabolic routing towards polyhydroxyalkanoic acid synthesis acid synthesis in recombinant *Escherichia coli* (fadR): inhibition of fatty acid β-oxidation by acrylic acid." FEMS Microbil. Lett. 167:89-94 (1998).

Sheng, et al., "Mechanistic studies of cyclohexanone monooxygenase: chemical properties of intermediates involved in catalysis," Biochemistry 40(37):11156-67 (2001).

Stafford, et al., "Metabolic engineering of indene bioconversion in *Rhodococcus* sp.," Adv. Biochem. Eng. Biotechnol. 73:85-101 (2001).

Stewart, "Organic transformations catalyzed by engineered yeast cells and related systems," Curr. Opin. Biotechnol. 11(4):363-8 (2000).

Tao, et al., "Altering toluene 4-monooxygenase by active-site engineering for the synthesis of 3-methoxycatechol, methoxyhydroquinone, and methylhydroquinone," J. Bacteriol. 186:4705-13 (2004).

Van Beilen, et al., "Cloning of Baeyer-Villiger monooxygenases from *Comamonas, Xanthobacter* and *Rhodococcus* using polymerase chain reaction with highly degenerate primers," Environ. Microbiol. 5(3):174-82 (2003).

Vardar et al., "Protein engineering of toluene-o-xylene monooxygenase from *Pseudomonas stutzeri* OX1 for enhanced chlorinated ethene degradation and o-xylene oxidation," Appl. Microbiol. Biotechnol. 68:510-7 (2005).

Vardar, et al., "Protein engineering of toluene-o-xylene monooxygenase from *Pseudomonas stutzeri* OX1 for oxidizing nitrobenzene to 3-nitrocatechol, 4-nitrocatechol, and nitrohydroquinone," J. Biotechnol. 115:145-56(2005).

Verho, R., et al., "Engineering redox cofactor regeneration for improved pentose fermentation in *Saccharomyces cerevisiae*." Appl Environ Microbiol. 69:5892-7(2003).

Wackett, "Directed evolution of new enzymes and pathways for environmental biocatalysis," Ann. N. Y. Acad. Sci. 864:142-52 (1998).

Walton et al., "An efficient enzymatic Baeyer-Villiger oxidation by engineered *Escherichia coli* cells under non-growing conditions," Biotechnol. Prog. 18(2):262-8 (2002).

Walton et al., "Understanding and improving NADPH-dependent reactions by nongrowing *Escherichia coli* cells," Biotechnol. Prog. 20(2):403-11 (2004).

Weckbecker et al., "Improved synthesis of chiral alcohols with *Escherichia coli* cells co-expressing pyridine nucleotide transhydrogenase, NADP+-dependent alcohol dehydrogenase and NAD+-dependent formate dehydrogenase," Biotechnol. Lett. 26:1739-44 (2004).

Willetts, "Structural studies and synthetic applications of Baeyer-Villiger monooxygenases," Trends Biotechnol. 15(2):55-62 (1997).

Zhu et al., "Effect of a single-gene knockout on the metabolic regulation in *Escherichia coli* for D-lactate production under microaerobic condition," Metab. Eng. 7:104-15 (2005).

\* cited by examiner

INCREASING NADPH-DEPENDENT PRODUCTS

CROSS-REFERENCE TO RELATED APPLICATIONS

This application is a 35 U.S.C. Section 371 of PCT/US2007/077163 filed Aug. 29, 2007, which claims priority to U.S. Provisional Application 60/823,829 filed Aug. 29, 2006, both incorporated herein by reference in their entirety.

FEDERALLY SPONSORED RESEARCH STATEMENT

This invention was made with government support under Grant No: BES-0000303 awarded by the National Science Foundation. The government has certain rights in the invention.

FIELD OF THE INVENTION

The invention relates to a technique for metabolically engineering *Escherichia coli* (*E. coli*) strains to deplete NAD-dependent glyceraldehyde-3-phosphate dehydrogenase and to simultaneously increase NADP-dependent glyceraldehyde-3-phosphate dehydrogenase (NADP-GAPDH). This provides increased intracellular NADPH availability by shifting the balance away from NADH production, and increases the yield and productivity of NADPH-dependent compounds.

BACKGROUND OF THE INVENTION

Numerous bioproducts including primary and secondary metabolites, recombinant proteins, and other biopolymers are produced by microbial fermentation. However, natural organisms are not optimized for this task, and product yield is often limited by NADPH or other metabolites. In order to improve bioproduct production, microorganisms may be engineered to enhance their metabolic capacity for chemicals such as NADPH.

The cofactor pair NADPH/NADP+ plays a central role as donors and/or acceptors of reducing equivalents during anabolic metabolism. The NADH/NAD+ pair alternatively is used primarily for catabolic activities of the cell. Together these cofactors influence virtually every oxidation-reduction metabolic pathway in the cell.

As one example, polyhydroxyalkanoates (PHAs) are a family of biodegradable polyesters synthesized by numerous microorganisms and function as an intracellular carbon and energy storage material. The best characterized PHA is polyhydroxybutyric acid (PHB). PHB is synthesized from acetyl-CoA in three sequential reaction steps catalyzed by the enzymes of the phb operon: β-ketothiolase, acetoacetyl-CoA reductase and PHB synthase, and the acetoacetyl-CoA reductase reaction requires NADPH as a cofactor. Due to the high cost and difficulty regenerating NADPH coenzymes, the enzymatic production of NADPH-dependent compounds such as PHB is challenging.

As a second example, three groups of FAD-dependent monooxygenases that use NADPH as a cofactor include flavin-containing monooxygenases (FAO), N-hydroxylating monooxygenases, and Baeyer-Villiger monooxygenases (BVMO). Enzymes of the BVMO type have been particularly interesting for their ability to form chiral lactone products from substituted cyclohexanones (Willetts, 1997; Stewart, 1998; Stewart, 2000), and an FAO enzyme that produces indigo has also been reported (Choi, 2003). Many BVMO enzymes have been isolated and mechanistic studies, 3-D structure and biochemical studies provides a detailed understanding of their reactions and allows their manipulation to produce desired products. The use of such enzymes in synthetic chemical processes and for the development of new drugs are of considerable importance, but the problem of limiting NADPH must be solved for these "green" resources to be commercially realized.

NADPH is normally generated through the oxidative part of the pentose phosphate pathway by the action of glucose-6-phosphate dehydrogenase (ZWF1):

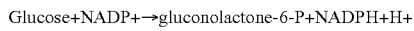

Glucose+NADP+→gluconolactone-6-P+NADPH+H+

Verho R, et al. (2003).

However, there are many other ways of generating NADPH. Fructose can be converted to mannitol, oxidizing two molecules of NAD(P)H using mannitol dehydrogenase and erythritol-4-phosphate dehydrogenase. Maicas, et al., (2002). Another protein that could be activated or overexpressed to increase NADP production is glucose dehydrogenase (GDH), per the following reaction:

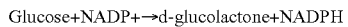

Glucose+NADP+→d-glucolactone+NADPH

Currently, several systems have been used to supply NADPH, including glucose dehydrogenase (Kataoka, 2003; Kizaki, 2001), alcohol dehydrogenase, and NADH-NADPH transhydrogenase. NADH-NADPH transhydrogenase is induced in *E. coli* strains following exposure to agents such as $H_2O_2$, however such methods are not useful due to the deleterious effects of the agents. Therefore, methods of increasing the intracellular levels of the cofactor NADPH are required that do not otherwise damage the cell or detract from its ability to produce large amounts of desirable product.

NADP-Dependent glucose dehydrogenases have been used for both bioproduction and NADPH generation in a continuous manner. Kizaki, et al. (2001) used *E. coli* cells expressing both the carbonyl reductase (S1) gene from *Candida magnoliae* and the glucose dehydrogenase (GDH) gene from *Bacillus megaterium* to synthesize enantiomeric ethyl (S)-4-chloro-3-hydroxybutanoate ((S)-CHBE) from ethyl 4-chloro-3-oxobutanoate (COBE). Liu, et al. (2005) have used a 2 cell system to perform a generation of ethyl (R)-4-chloro-3-hydroxybutanoate, but cell extracts were used in a non-renewing system with one cell expressing an NADPH-dependent aldehyde reductase gene for the asymmetric reduction of ethyl 4-chloro-3-oxobutanoate and a second cell expressing glucose dehydrogenase gene for NADPH generation. These systems demonstrate the benefits of bacterial NADPH production and use of NADPH dependent enzymes to generate relevant compounds. But stoichiometric amounts of cofactor are required and these systems lack a continuous, high level production of NADPH that is required to allow these reactions to proceed.

The present invention provides methods to increase intracellular availability of NADPH, allowing the increase of products that require this cofactor in their biosynthesis pathways. An example is the production of polyhydroxybutyrate. Other applications are the production of amino acids, lycopene, lactones, chiral alcohols, pharmaceutical intermediates and other biosynthetic products. The system will work with a variety of carbon source feed stocks for applications from bioproduction to bioremediation.

SUMMARY OF THE INVENTION

A method of producing NADPH-dependent bacterial products is described where the levels of NADPH in the cell are increased by decreasing the activity of NADH-dependent GAPDH (NAD-GAPDH) activity and increasing NADPH-dependent GAPDH (NADP-GAPDH) activity.

Engineered bacterial cells are described that have reduced NAD-GAPDH activity and increased NADP-GAPDH activity (NADP+ cells). These engineered cells provide a background for increased production of NADPH dependent products such as PHAs, PHBs, lycopenes, lactones, chiral alcohols, pharmaceutical intermediates and other biologically produced compounds. The cell will produce at least 30% more NADPH after engineering than it did before engineering. In preferred embodiments, it will produce at least 40% more, or 50% more NADPH.

In certain embodiments of the invention, NAD-GAPDH activity is reduced by inhibition or inactivation. In a preferred embodiment, NAD-GAPA is inactivated by recombination, mutation, deletion, or truncation.

In other embodiments of the invention, NADP-GAPDH activity is increased by overexpression. Overexpression may be achieved by expressing an exogenous NADP-GAPDH. Examples of suitable NADP-GAPDH proteins include but are not limited to *Clostridium* GAPN, *Saccharomyces* GAPDH, *Mycoplasma* GAPDH, *Streptococcus* GAPDH, and *Synechococcus* GAPDH.

In one embodiment of the invention, an engineered NADP+ cell incorporates an NADPH-dependent pathway for bioproduction of a compound. Incorporated enzymes may be selected from the phb operon (β-ketothiolase, acetoacetyl-CoA reductase and PHB synthase); lycopene synthesis (crtE, B, I, and y); monooxygenases (including FAOs and BVMOs); carbonyl reductases (CBR); as well as various oxidoreductases, dehydrogenases and synthase proteins. FMN reductase, glutamate synthase, and butanol dehydrogenase represent this broad class of NADPH-dependent enzymes of which approximately 2500 varieties are publicly available from the NCBI™ protein database (www.ncbi.nlm.nih.gov) incorporated herein by reference.

DESCRIPTION OF EMBODIMENTS OF THE INVENTION

Figure 1:
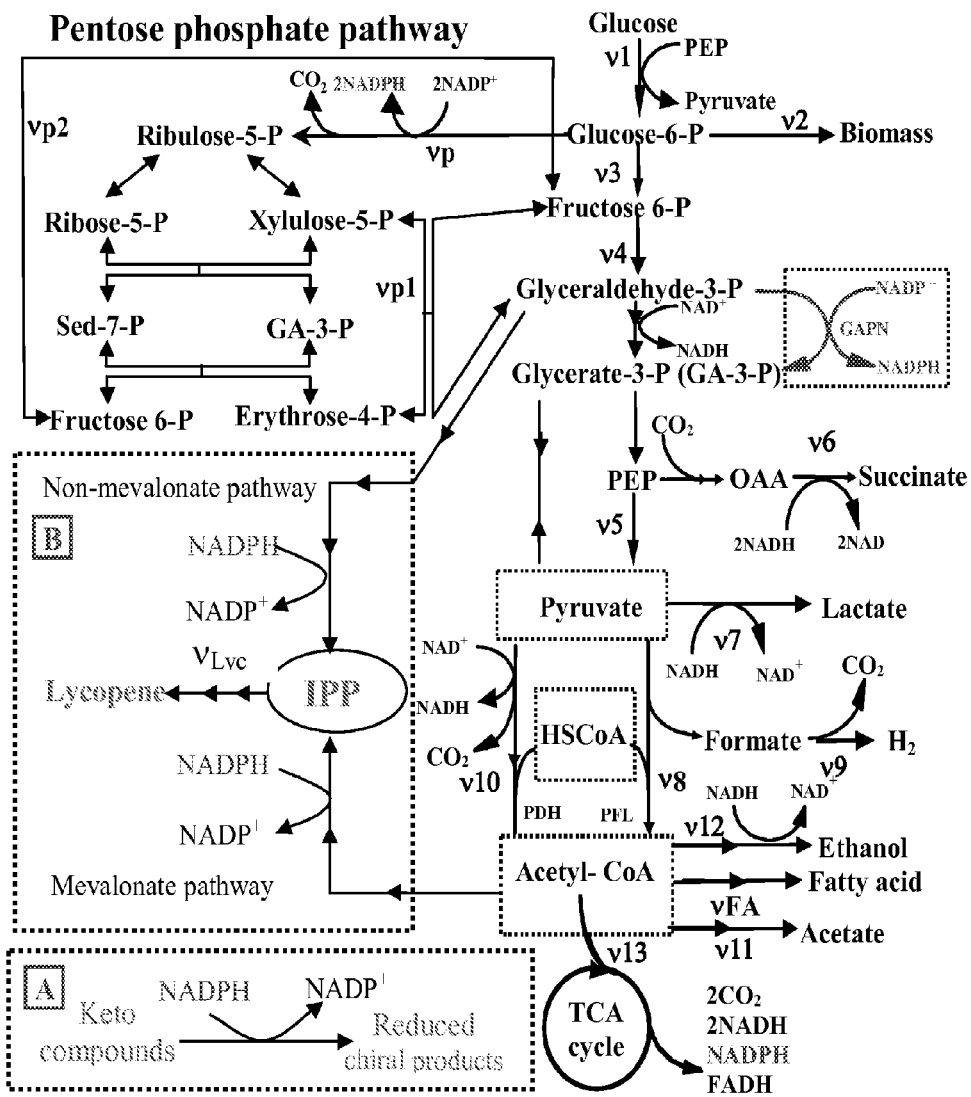
FIG. 1: Central pathway showing native NAD-GAPDH replaced with NADP-GAPDH.
Figure 2:
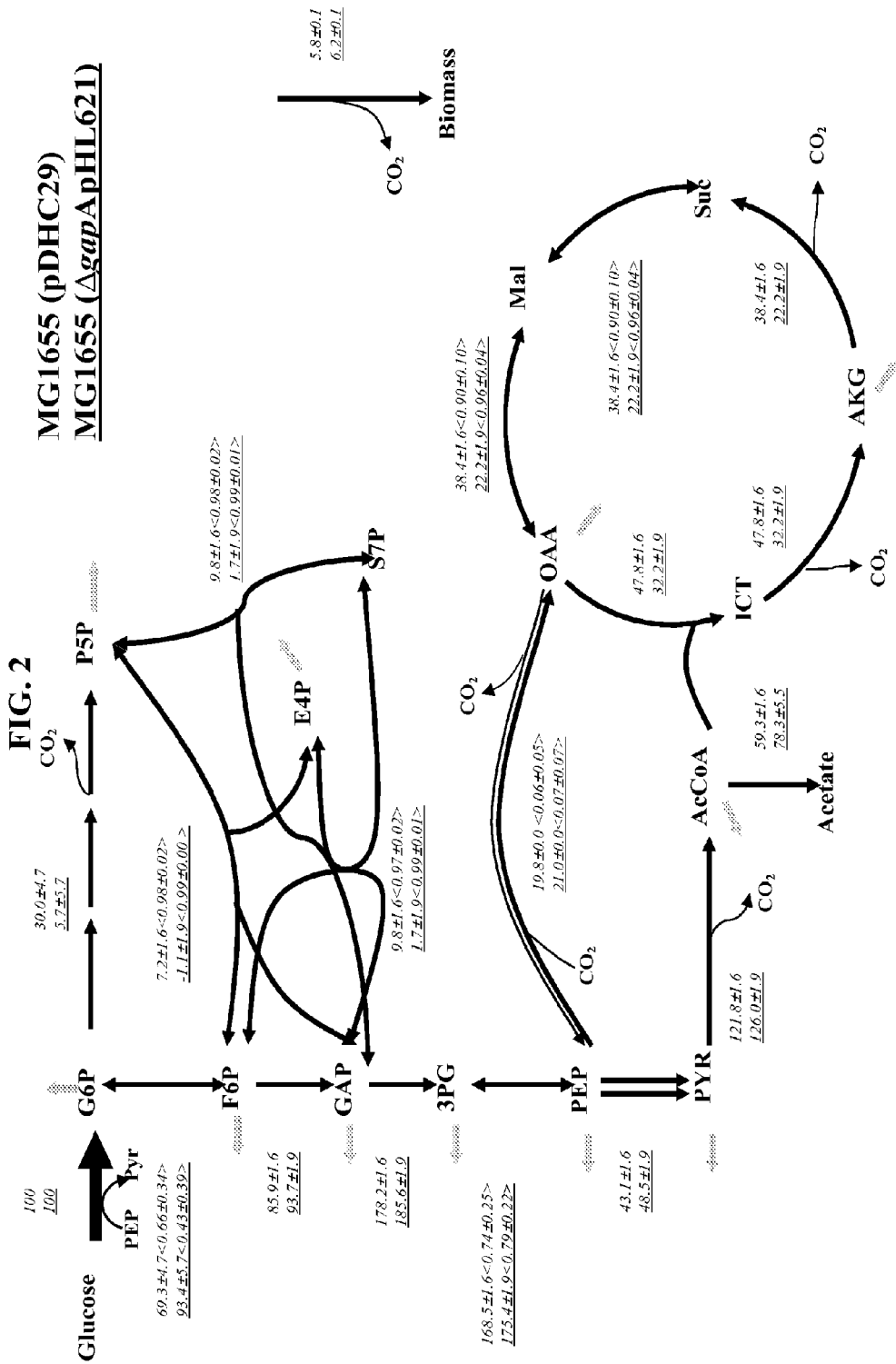
FIG. 2: Metabolic Flux Distribution with wt NAD cells and NADP+ Cells.

The invention relates to the construction of genetically engineered bacterial strains capable of increasing intracellular NADPH availability directly from reducing equivalents of NADH. By decreasing NAD-GAPDH activity and increasing NADP-GAPDH activity, NADPH is produced during glycolysis in lieu of NADH. NAD-GAPDH activity can be decreased by specific inhibitors, mutation, disruption, truncation, or deletion. NADP-GAPDH activity can be increased with enhancers, by overexpression, and stable chromosomal integration.

NADPH molar yield can be further increased by combining an NADPH-dependent glucose-6-phosphate and an NADPH-dependent GAPDH. Levels of NADP-dependent product are manipulated by changing the expression levels of selected enzymes and/or the quantity of supplied substrate. In one example, increasing NADP-GAPDH and glucose subsequently increases production of NADPH.

Cell strains with increased NADPH production allow more efficient and greater amounts of NADP-dependent products. NADP-dependent products include carboxylic acids, amino acids, acetate, lycopene and other biosynthetic products; biodegradation of toxic chemicals; and synthesis of desired proteins. In one embodiment, PHB is produced by transforming a NADPH-GAPDH cell strain with a phb operon containing plasmid and culturing said cells with glucose. By combining increased NADPH-GAPDH cell strains with monooxygenase expression, stereospecific chiral compounds are synthesized. In one embodiment, linear aliphatic ketone esters are generated.

Carboxylic acids described herein can be a salt, acid, base, or derivative depending on structure, pH, and ions present. For example, the terms "succinate" and "succinic acid" are used interchangeably herein. Succinic acid is also called butanedioic acid ($C_4H_6O_4$). Chemicals used herein include formate, glyoxylate, lactate, malate, oxaloacetate (OAA), phosphoenolpyruvate (PEP), and pyruvate. Bacterial metabolic pathways including the Krebs cycle (also called citric acid, tricarboxylic acid, or TCA cycle) can be found in Principles of Biochemistry, by Lehninger as well as other biochemistry texts.

PHAs are mainly composed of R-(−)-3-hydroxyalkanoic acid monomers that can be broadly subdivided into two groups: short chain PHAs consisting of 3 to 5 carbon monomers (C3-C5) and long chain PHAs consisting of 6 to 14 carbon monomers (C6-C14) or more. PHAs such as PHB are produced as monomers and polymers. 4-carbon acids, salts, and derivatives of butyric acid can be present depending on the structure, pH, and ions present. Polyesters can be synthesized by allowing PHAs to crosslink under various conditions. PHAs have the general formula:

TABLE 1

PHA NOMENCLATURE $$\left[ \begin{array}{c} R_1 \quad O \\ \diagdown\diagup \diagdown\diagup\diagdown \\ O \qquad (CH_2)_n \end{array} \right]_X$$

| $R_1$ | n | IUPAC Name | Abbreviation |
|---|---|---|---|
| Hydrogen | 1 | 3-hydroxypropionate | (3HP) |
| Methyl | 1 | 3-hydroxybutyrate | (3HB) |
| Ethyl | 1 | 3-hydroxyvalerate | (3HV) |
| Propyl | 1 | 3-hydroxycaproate | (3HC) |
| Butyl | 1 | 3-hydroxyheptanoate | (3HH) |
| Pentyl | 1 | 3-hydroxyoctanoate | (3HO) |
| Hexyl | 1 | 3-hydroxynonanoate | (3HN) |
| Heptyl | 1 | 3-hydroxydecanoate | (3HD) |
| Octyl | 1 | 3-hydroxyundecanoate | (3HUD) |
| Nonyl | 1 | 3-hydroxydodecanoate | (3HDD) |
| Hydrogen | 2 | 4-hydroxybutyrate | (4HB) |
| Methyl | 2 | 4-hydroxyvalerate | (4HV) |
| Ethyl | 2 | 4-hydroxycaproate | (4HC) |
| Octyl | 2 | 4-hydroxydodecanoate | (4HDD) |
| Hydrogen | 3 | 5-hydroxyvalerate | (5HV) |
| Methyl | 3 | 5-hydroxycaproate | (5HC) |
| Hydrogen | 10 | 12-hydroxydodecanoate | (12HDD) |

By counting the distance from the carbonyl to the oxygen, one obtains the chain length. For the first ten compounds in TABLE 1 the carbonyl is three carbons from the oxygen. By counting the total number of carbons, one gets the compound name. Proprionate has three carbons, butyrate has four carbons, valerate has five carbons, caproate has six carbons, and so on. PHAs are synthesized by PHA synthases from a variety of organism. Each organism produces specific PRAs and unique PHA synthase genes have been found in *Pseudomonas aeruginosa* (Lagenbach, et al., 1997; Qi, et al., 1997; Qi, et al., 1998).

"Metabolic engineering" is the targeted and purposeful alteration of metabolic pathways found in an organism in order to use cellular pathways for chemical transformation, energy transduction, and supramolecular assembly.

The terms "operably associated" or "operably linked," as used herein, refer to functionally coupled nucleic acid sequences.

"Reduced activity" is defined herein to be at least a 75% reduction in protein activity, as compared with an appropriate control species. Preferably, at least 80, 85, 90, 95% reduction in activity is attained, and in the most preferred embodiment, the activity is eliminated (100%) ("inactivated"). Protein activity can be reduced or completely inactivated with inhibitors, by mutation, or by suppression of expression or translation, and the like. By "null mutant" or "null mutation" what is meant is that activity is completely inactivated. In one example, the control plasmid is inserted without the gene of interest. In another example the gene of interest is completely removed by recombination. Additionally, the gene of interest may be removed by inactivation, mutation, or truncation which eliminates activity.

"Overexpression" or "overexpressed" is defined herein to be greater than wild type activity, preferably above 125% increase, more preferably above 150% increase in protein activity as compared with an appropriate control species. Preferably, the activity is increased 100-500%. Overexpression is achieved by mutating the protein to produce a more active form, a more stable form, or a form that is resistant to inhibition, by removing inhibitors, or adding activators, and the like. Overexpression can also be achieved by removing repressors, adding multiple copies of a gene to the cell, up-regulating an existing gene, adding an exogenous gene, and the like.

The terms "disruption" and "disruption strains," as used herein, refer to cell strains in which the native gene or promoter is mutated, deleted, interrupted, or down-regulated in such a way as to eliminate the activity of the gene. A gene is completely (100%) reduced by knockout or removal of the entire genomic DNA sequence. Use of a frame shift mutation, early stop codon, point mutations of critical residues, or deletions or insertions, and the like, can completely inactivate (100%) gene product by completely preventing transcription and/or translation of active protein.

The term "exogenous" indicates that the protein or nucleic acid is a non-native molecule introduced from outside the organism or system, without regard to species of origin. For example, an exogenous peptide may be applied to the cell culture, an exogenous RNA may be expressed from a recombinant DNA transfected into a cell, or a native gene may be under the control of exogenous regulatory sequences.

As used herein "recombinant" is relating to, derived from, or containing genetically engineered material.

A gene or cDNA may be "optimized" for expression in *E. coli*, or other bacterial species using the codon bias for the species. Various nucleotides can encode a single peptide sequence. Understanding the inherent degeneracy of the genetic code allows one of ordinary skill in the art to design multiple nucleotides which encode the same amino acid sequence. NCBI™ provides codon usage databases for optimizing DNA sequences for protein expression in various species.

There are over 6000 GAPDH proteins available in the GenBank™ database. *Saccharomyces cerevisiae* NADP+-dependent GAPDH (GDP1) and *Clostridium acetobutylicum* GAPDH (GAPC) are two examples of many GAPDH enzymes. Amino acid identity within the GAPDH family from various kingdoms, genus, and species ranges contiguously from about 50%-100% identity. Non-limiting examples of GAPDH proteins are listed in Table 2.

TABLE 2

GAPDH PROTEINS FROM VARIOUS SPECIES

| Acc # | Species | Cofactor |
|---|---|---|
| NP_416293 | *Escherichia coli* strain K12 GAPA | NAD |
| NP_754078 | *Escherichia coli* strain CFT073 GAPA | NAD |
| NP_310515 | *Escherichia coli* strain O157:H7 GAPA | NAD |
| NP_707335 | *Shigella flexneri* GAPA | NAD |
| NP_460256 | *Salmonella typhimurium* GAPA | NAD |
| NP_993297 | *Yersinia pestis* GAPA | NAD |
| NP_231634 | *Vibrio cholerae* GAPA | NAD |
| NP_873724 | *Haemophilus ducreyi* GAPA | NAD |
| NP_245861 | *Pasteurella multocida* GAPDH | |
| NP_438174 | *Haemophilus influenzae* GAPDH | |
| NP_596154 | *Schizosaccharomyces pombe* GDP1 | |
| NP_001009307 | *Felis catus* GAPDH | |
| NP_058704 | *Rattus norvegicus* | NAD |
| NP_002037 | *Homo sapiens* GAPD | NAD |
| YP_082354 | *Bacillus cereus* GAPN | NADP |
| NP_896125 | *Synechococcus* GAP2 | NADP |
| NP_975495 | *Mycoplasma mycoides* GAPN | NADP |
| NP_893861 | *Prochlorococcus marinus* GAP2 | NADP |
| NP_721104 | *Streptococcus mutans* GAPN | NADP |
| NP_440929 | *Synechocystis* GAP1 | |
| NP_442821 | *Synechocystis* GAP2 | |
| NP_178071 | *Arabidopsis thaliana* GAPDH | NAD |
| NP_566796 | *Arabidopsis thaliana* GAPA | NADP |
| NP_174996 | *Arabidopsis thaliana* GAPB | NADP |
| NP_347346 (SEQ ID NO 1) | *Clostridium acetobutylicum* GAPDH | |
| NP_562220 | *Clostridium perfringens* GAPDH | |
| NP_563354 | *Clostridium perfringens* GAPN | NADP |
| NP_984891 | *Eremothecium gossypii* TDH3 | |
| NP_012483 | *Saccharomyces cerevisiae* TDH1 | |
| NP_012542 | *Saccharomyces cerevisiae* TDH2 | |
| NP_011708 | *Saccharomyces cerevisiae* TDH3 | |

In certain embodiments of the invention, proteins from other species may also be used. For example, NADPH-dependent GAPDH from *Saccharomyces, Synechocystis*, or other species may be optimized for expression in *E. coli, Clostridium*, or other host strain. Many other NAD-GAPDH and NADP-GAPDH are identified by using BLAST™ with reference NAD-GAPDH and NADP-GAPDH nucleotide or amino acid sequences. NAD-GAPDH and NADP-GAPDH activity is confirmed by similarity in sequence and function. GAPDH activity assays differentiate between NAD- and NADPH-dependent GAPDH proteins. By assaying a GAPDH in the presence of either NAD(+) or NADP(+) and monitoring the change in absorbance of one or both of these cofactors, the NAD- or NADP-dependence of the GAPDH enzyme is determined.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova T A & Madden T L (1999) FEMS Microbiol. Lett. 174:247-250. The default parameters were used, except the filters were turned OFF. As of Jan. 1, 2001 the default parameters were as follows: BLASTN or BLASTP as appropriate; Matrix=none for BLASTN, BLOSUM62 for BLASTP; G Cost to open gap default=5 for nucleotides, 11 for proteins; E Cost to extend gap [Integer] default=2 for nucleotides, 1 for proteins; q Penalty for nucleotide mismatch [Integer] default=−3; r reward for nucleotide match [Integer] default=1; e expect value [Real] default=10; W word size [Integer] default=11 for nucleotides, 3 for proteins; y Dropoff (X) for blast extensions in bits (default if zero) default=20 for blastn, 7 for other programs; X dropoff value for gapped alignment (in bits) 30 for blastn, 15 for other programs; Z final X dropoff value for gapped alignment (in bits) 50 for blastn, 25 for other programs. This program is available online at NCBI™ (www.ncbi.nlm.nih.gov/BLAST/).

"Bacteria" as used herein refer to *E. coli, L. lactis, P. aeruginosa*, and other strains that are publicly available. ATCC®, AMERICAN TYPE CULTURE COLLECTION™ (www.atcc.org) has an extensive collection of cell strains that are publicly available and incorporated herein by reference. The NCBI™ web site has numerous codon bias charts available for allowing protein expression in most species. Plasmids are available that can be transferred between bacterial species or used in multiple species, sometimes called shuttle vectors. Thus methods developed in *E. coli* are applicable to any bacterial species using tools known to one of ordinary skill in the arts.

Common restriction enzymes and restriction sites are found at NEB® (NEW ENGLAND BIOLABS®, www.neb.com) and INVITROGEN® (www.invitrogen.com).

TABLE 3

ABBREVIATIONS

| Abbr | Term |
|---|---|
| 3PG | 3-phosphoglycerate |
| AKG | α-ketoglutarate |
| Ap | ampicillin |
| ApR | ampicillin resistance |
| ATCC ® | American Tissue-type Culture Collection |
| BVMO | Baeyer-Villiger monooxygenases |
| CBR or CR | carbonyl reductase |
| (S)-CHBE | ethyl (S)-4-chloro-3-hydroxybutanoate |
| Cm | chloramphenicol |
| Cn | carbenicillin |
| COBE | ethyl 4-chloro-3-oxobutanoate |
| ColE1 | gram-negative origin of replication |
| crtB | phytoene synthase |
| crtE | GGDP synthase |
| crtI | phytoene desaturase |
| crtY | β-end lycopene cyclase |
| E4P | erythrose-4-phosphate |
| Em | erythromycin |
| F6P | fructose-6-phosphate |
| FAO | flavin-containing monooxygenases |
| FDH | FMN dehydrogenase |
| FMN | flavin mononucleotide |
| G6P | glucose-6-phosphate |
| GAP | glyceraldehyde phosphate |
| GAPA | NAD-dependent GAPDH |
| GAPC | NADP-dependent GAPDH |
| GC-MS | gas chromatography-mass spectroscopy |
| GDH | glucose dehydrogenase |
| ICT | isocitrate |
| Km | kanamycin |
| KmR | kanamycin resistance |
| Mal | malate |
| MLSR | macrolide, lincosamide and streptogramin A resistance |
| MTBSTFA | methyl-N-(tert-butyl-dimethylsilyl) trifluoroacetamide |
| NAD-GAPDH | NAD-dependent glyceraldehyde-3-phosphate dehydrogenase |
| NAD Cells | wt NAD-GAPDH cells (control) |

TABLE 3-continued

ABBREVIATIONS

| Abbr | Term |
|---|---|
| NADP-GAPDH | NADP-dependent glyceraldehyde-3-phosphate dehydrogenase |
| NADP+ Cells | NAD-GAPDH cells with + NADP-GAPDH |
| Nal | nalidixic acid |
| NCBI ™ | National Center for Biotechnology Information |
| OAA | oxaloacetate |
| OriII | Gram-positive origin of replication |
| Ox | oxacillin |
| P5P | pentose phosphate |
| PEP | phosphoenolpyruvate |
| PHA | polyhydroxyalkanoate |
| PHB | polyhydroxybutyric acid |
| PNT | pyridine nucleotide transhydrogenase |
| PYR | pyruvate |
| S7P | Sedoheptulose-5-phosphate |
| Sm | streptomycin |
| $Sm^R$ | streptomycin resistance |
| Suc | succinate |
| Tc | tetracycline |
| $Thi^R/Cm^R$ | thiamphenicol/chloramphenicol resistance |
| tsBVMO | thermostable BVMO |
| wt | wild-type |

Plasmids and strains used in certain embodiments of the invention are set forth in Table 4.

TABLE 4

PLASMIDS AND STRAINS

| Plasmid/Strain | Genotype | Ref |
|---|---|---|
| pDHC29 | Cloning vector $Cm^R$ | Phillips, 2000 |
| pHL621 | pDHC29 with *C. acetobutylicum* gapC | This work |
| pMM4 | BVMO plasmid | Walton, 2002 |
| pTSBVMO | Thermostable BVMO | (in process) |
| pACYC184 | crtE, crtI, crtB lycopene genes | Cunningham, 1994 |
| pPHB | phb operon | This work |
| pPNT/FDH | pnt and NADP-fdh | (in process) |
| pFDH | NADP-fdh | (in process) |
| pHL621+ | pHL621 with NADP-fdh | This work |
| MG1655 | Wild type (F-λ-) | Guyer, 1988 |
| ΔGAPA | MG1655 ΔgapA | This work |
| GAPA+ (control) | MG1655 pDHC29 w/ NAD-GADPH | This work |
| NADPH+ | ΔGAPA pHL621 (NADP-GADPH) | This work |
| NADPH++ | ΔGAPA pHL621 pPNT/FDH | (in process) |
| Lycopene+ | NADPH+ pACYC18 | This work |
| Lactone+ | NADPH+ pMM4 | This work |
| tsLactone+ | NADPH+ pTSBVMO | (in process) |
| PHB+ | NADPH+ pPHB | This work |
| Lycopene++ | NADPH++ pACYC18 | This work |
| Lactone++ | NADPH++ pMM4 | This work |
| tsLactone++ | NADPH++ pTSBVMO | (in process) |
| PHB++ | NADPH++ pPHB | (in process) |

When plasmids are used, the effect of host/plasmid interaction is minimized by comparing three different systems consisting of: the host only, a plasmid expressing biologically active enzyme, and a control system with the expression vector alone.

Standard fermentations in a well-controlled bioreactor are conducted for all in vivo experiments. For aerobic experiments, the dissolved oxygen concentration is controlled by either changing the agitation speed or bubbling with enriched air through an automatic dissolved oxygen controller. The pH of the fermentor is maintained at a constant level by the addition of HCl or NaOH. For chemostat experiments, the experimental data are collected during the steady state (with respect to the biomass and fermentation products), usually after 5 to 7 residence times.

The effect of genetic and environmental perturbations on metabolic and gene expression patterns is assessed by monitoring the extracellular metabolite concentrations, intermediate metabolite concentrations, and key enzymatic activities. Hexoses and fermentation products are measured by high-performance liquid chromatography (HPLC) using a specialized column (Vallino and Stephanopoulos 1993; Yang et al., 1999a). A BIO-RAD® AMINEX HXP-87H™ column specially designed for the analysis of small molecules is used to quantify chemical compounds. Fermentation products quantified include succinic acid, lactic acid, formic acid, acetic acid, pyruvate, glucose, and ethanol. Glucose, acetic acid and lactic acid are measured by commercially available enzymatic assays to supplement HPLC measurements. Oxygen and carbon dioxide in the off-gas is measured on-line using an oxygen/carbon dioxide analyzer (NEW BRUNSWICK SCIENTIFIC®, Edison, N.J.).

For intracellular compound measurements, samples are quenched immediately in a centrifuge tube containing a quenching solution (−80° methanol solution, Zhu & Shimizu, 2005). The intracellular concentrations of CoA, acetyl-CoA, are measured by HPLC (Vadali et al., 2002a; Boynton et al., 1996) using a C-18 column and a UV detector. NADP+/NADPH levels are measured by HPLC chromatography (Boada et al., 2000; Tian et al., 1998; Shalel Levanon, et al., 2005).

In experiments where a detailed analysis is performed, the activities of certain key enzymes in the metabolic pathways can be measured. These enzymes include GAPDH or GAPN (Tamoi et al., 1996; Iddar et al., 2002), FDH (Berrios-Rivera et al., 2002a,b), transhydrogenase (Boonstra et al., 1999), BVMO (Walton & Stewart 2004), and others.

EXAMPLE 1

Flux Analysis with NADPH-GAPDH Strains

Glucose-limited chemostat cultures of *E. coli* GAP+ and NADPH+ strains were studied at a dilution rate of 0.35±0.02 $h^{-1}$ in 1-L bioreactors (BIOFLO 110™, NEW BRUNSWICK SCIENTIFIC®, Edison, N.J.). A modified M-9 media was used for the cultivations and 20 mM of glucose was used as a sole carbon source. The working volume was maintained at 600 ml, and the cultivation temperature was kept at 37° C. The pH value was maintained at 7.0±0.04 by titrating with 3 M NaOH and 1.5 M of $HNO_3$. Aerobic culture conditions were controlled by purging the bioreactor with air at a rate of 2 ml/min and keeping the agitation speed at 285 rpm. Labeling experiments were started after 8 resident times when the cultures reached steady state. The unlabeled feeding media was replaced by an identical M9 media containing 16 mM unlabeled glucose, 2 mM [U-13C] glucose, and 2 mM [1-13C] glucose. Cell pellets in 50 ml of culture broth were harvested after another residence time by centrifugation. The extracellular metabolite concentrations were measured using a HPLC (table 1). The cell pellets were washed and then hydrolyzed in 6 ml of 6 M HCl for 12 h at 105° C. The hydrolysate was filtered, dried, and then derivatized using N-Methyl-N-(tert-butyl-dimethylsilyl)trifluoroacetamide (MTBSTFA) (Christensen and Nielsen, 1999). The derivatized proteinogenic amino acids were measured using GC-MS (GCMS-QP2010™, SHIMADZU®, Tokyo) to determine the isotopomer distribution. The metabolic flux distributions in the cells were estimated using a MATLAB™ (The MATHWORKS®, Natick, Mass.) program based on the measured metabolite concentrations and isotopomer distributions of the amino acids. The results of the metabolic flux distribution analysis are shown in FIG. 1.

TABLE 5

EXTRACELLULAR METABOLITE CONCENTRATIONS

| System | Cell Biomass Conc. (g/L) | Initial glucose Conc. (mM) | Residual glucose conc. (mM) | Specific glucose uptake rate (mM/gDCW/h) | Acetate conc. (mM) |
|---|---|---|---|---|---|
| GAPA+ | 0.97 ± 0.03 | 19.62 ± 0.10 | 2.94 ± 0.16 | 5.99 ± 0.05 | 9.88 ± 0.22 |
| NADPH+ | 1.07 ± 0.03 | 19.28 ± 0.19 | 2.01 ± 0.13 | 5.67 ± 0.04 | 13.51 ± 1.06 |
| % Change | 110% | | 68% | 95% | 137% |

The flux analysis of carbon through the NAD-GAPDH and NADP-GAPDH engineered bacteria indicate that production was shifted from P5P and other products to acetate. The NADP-GAPDH system produced more acetate and converted more glucose to acetate than did the NAD-GAPDH (See Table 6). Aerobic acetate production in *E. coli* is beneficial, because *E. coli* grow better under aerobic than anaerobic conditions thus allowing greater acetate production.

TABLE 6

METABOLIC FLUX DISTRIBUTION

| Metabolite | GAPA+ | NADPH+ | Δ | % Increase | NADPH Produced |
|---|---|---|---|---|---|
| Glucose | 100 | 100 | 0 | 0 | |
| Glucose-6-Phosphate (G6P) | 69.3 ± 4.7 | 93.4 ± 5.7 | 24.1 | 40% | |
| Fructose 6 Phosphate (F6P) | 85.9 ± 1.6 | 93.7 ± 1.9 | 7.8 | 11% | |
| (P5P) | 30.0 ± 4.7 | 5.7 ± 5.7 | −24.3 | −75% | |
|  | 7.2 ± 1.6 | −1.1 ± 1.9 | −8.3 | −145% | |
| (E4P)/(S7P) | 9.8 ± 1.6 | 1.7 ± 1.9 | −8.1 | −101% | |

TABLE 6-continued

METABOLIC FLUX DISTRIBUTION

| Metabolite | GAPA+ | NADPH+ | Δ | % Increase | NADPH Produced |
|---|---|---|---|---|---|
| Glyceraldehyde Phosphate (GAP) | 178.2 ± 1.6 | 185.6 ± 1.9 | 7.4 | 5% | |
| 3-Phosphoglycerate (3PG) | 168.5 ± 1.6 | 175.4 ± 1.9 | 6.9 | 5% | |
| Phosphoenolpyruvate (PEP) | 43.1 ± 1.6 | 48.5 ± 1.9 | 5.4 | 16% | |
| Pyruvate (PYR) | 121.8 ± 1.6 | 126.0 ± 1.9 | 4.2 | 4% | |
| Acetyl CoA | 59.3 ± 1.6 | 78.3 ± 5.5 | 19.0 | 32% | |
| Isocitrate (ICT) | 47.8 ± 1.6 | 32.2 ± 1.9 | −15.6 | −30% | |
| α-ketoglutarate (AKG) | 38.4 ± 1.6 | 22.2 ± 1.9 | −16.2 | | |
| Succinate (Suc)/Malate (Mal) | 38.4 ± 1.6 | 22.2 ± 1.9 | −16.2 | −38% | |
| Oxaloacetate (OAA) | 47.8 ± 1.6 | 32.2 ± 1.9 | −15.6 | 6% | |
| Acetate | 59.3 ± 1.6 | 78.3 ± 5.5 | 19.0 | 32% | |

EXAMPLE 2

Integration of NADP-GAPDH

We have shown that it is possible to increase the in vivo NADH availability by overexpressing the NAD-dependent formate dehydrogenase in *E. coli* (Berríos-Rivera et al., 2002a; 200b). Excess NADH can be converted by PNT to NADPH that in turn is used for biosynthesis of NADPH-dependent compounds.

PNTs catalyze the reversible transfer of reducing equivalents between NAD and NADPH pools through the following reaction:

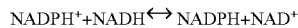

Two groups of transhydrogenases (AB and BB transhydrogenases) have been defined and cloned from a number of organisms including humans (Arkblad et al., 1996) and mice (Arkblad et al., 1996) as well as bacteria from *E. coli* (Clarke et al., 1986) to *Rickettsia* (Ogata, 2001) and *Rhodospirillum* (Williams et al., 1996). We have previously shown that the soluble transhydrogenase UdhA from *E. coli* (Boonstra et al., 1999) has a beneficial effect on PHB productivity. The recycling system is further enhanced by the membrane-bound transhydrogenase PntAB (Clarke et al., 1986). Plasmids expressing udhA or pnt under the pBAD promoter can be constructed and characterized as previously described. These host/plasmid systems are then evaluated for NADPH availability by analyzing their ability to form the lactone product in the presence of a BVMO construct (see below).

EXAMPLE 3

Coexpressing PNT & FDH

Transhydrogenase constructs integrated with existing NADH recycling systems (Berríos-Rivera et al., 2002a; 200b) will further increase NADPH production. Formate derived from the cell culture medium, as is commonly observed in lycopene production processes or supplemented externally (Berríos-Rivera et al., 2002a; 200b), is converted to NADH in the presence of FDH. This coupled system uses reducing power from formate to generate NADPH through two enzymatic systems, the NAD-dependent formate dehydrogenase and a transhydrogenase. Alternatively, an NADPH-dependent FDH can generate NADPH from formate. Example FDHs are described and known to one of ordinary skill in the art (Tishkov & Popov, 2004). By adding a PNT enzyme, residual NADH is converted to NADPH further increasing the molar yield of bioproducts.

EXAMPLE 4

Overexpressing NADP-Dependent GAPDH

Stable ΔgapA bacterial strains with NADPH-GAPDH integration are created using P1 phage transduction and the one-step inactivation based on λ red recombinase (Datsenko and Wanner, 2000). Briefly, the *C. acetobutylicum* gapC gene is cloned under the control of the pBAD promoter. The gapC gene with its associated pBAD promoter is cloned into pKD4 adjacent to the removable Km marker. The function of each gene is verified by enzyme assay of extracts from gapA mutant hosts bearing the pKD4 gapC plasmid. The Km-gapC segment is amplified by PCR and recombined into the gapA gene on the chromosome of *E. coli*. The Km marker is removed by the site specific recombination. The strain is evaluated compared to an isogenic gapA+ parent strain in its ability to process cyclohexanone substrates to the lactone product. The stable NADP-GAPDH strain is useful as a background for product production and is desirable for batch or continuous-flow fermentations.

Use of an altered gapC gene in other strains (e.g. the previously reported host for BVMO studies) demonstrates the robust nature of the NADPH production system and the ability to increase NADPH-dependent products in other backgrounds. The enzymes of the phb operon β-ketothiolase, acetoacetyl-CoA reductase and PHB synthase can be incorporated with NADP-GAPDH in one transposon or transformed into a stable NADP-GAPDH strain to create a stable PHB synthesis strain. Thus integration of the NADPH dependent gapC creates a stable background for bioproduction.

Figure 3:
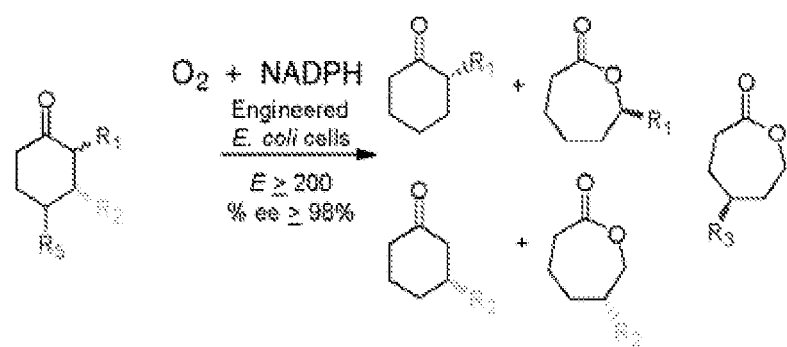
FIG. 3: PHB production in NADPH+ bacteria.

FIG. 3 demonstrates PHB production in NADH control cells [MG1655 (pDHC29 pPHB)] and NADPH+ production cells [MG1655 ΔgapA (pHL621 pPHB)]. NADPH+ produced 5-10 fold greater PHB than wild type controls. This demonstrates the increased production achieved with increased NADPH flux.

EXAMPLE 5

Additional Modifications

Other NADPH forming enzymes can be introduced into *E. coli* through the replacement of the native malate dehydrogenase (mdh) and pyruvate dehydrogenase (pdh) genes (both native enzymes are NADH utilizing enzymes) with genes encoding mutant forms that have a high preference for NADPH. Such enzymes that function in *E. coli* have been described (Issakidis et al., 1993; Bocanegra et al., 1993), however their effects on metabolism or pathway fluxes will have to be evaluated. The NADPH-dependent PDH enzyme has been engineered by introducing 7 mutations and the Km, kcat, and kcat/Km compared favorably with those of the wild-type enzyme with its native NAD cofactor (Bocanegra et al., 1993). Introduction of this construct into the E. coli chromosome will replace the native pdh gene as described for the gapC construction. The strain can then be studied and compared with the gapC replacement strain and the NADPH-dependent-pdh and the NADPH-dependent gapC can be combined in one host to produce up to 6 NADPH from one glucose.

Alternative TCA cycle enzymes can be replaced with a NADPH-dependent enzyme, including malate dehydrogenase that catalyzes the conversion of malate to oxaloacetate. A triple cysteine mutant of sorghum leaf NADP-malate dehydrogenase has been constructed and over-expressed in E. coli, to yield constitutive dithiol-insensitive enzyme. This enzyme did not require thioredoxin for function and was well expressed in E. coli. Replacement of the native mdh gene as described will create the NADPH-dependent mdh strain. A NADPH-dependent mdh and variants of the NADPH-dependent gapC strain can be combined for testing of a strain that could produce even more NADPH from one glucose. In these excess-NADPH producing strains, a "sink" for excess reductant may be provided by an alcohol dehydrogenase or BVMO system converting a excess NADPH to a valuable chemical. Strains with excess NADPH and several pathways for NADPH biosynthesis will remove reaction rate limitations and increase the amount of NADPH produced per glucose.

EXAMPLE 6

Chiral Compound Production

Native NAD+-dependent glyceraldehyde-3-phosphate dehydrogenases (GAPDH) was replaced with C. acetobutylicum (gapnN) NADP+-dependent glyceraldehyde-3-phosphate dehydrogenase for the conversion of cyclohexanone to ε-caprolactone.

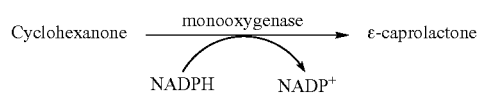

The control strain GAPA+ [BL21(pDHC29, pMM4)] harbors the control null vector pDHC29 which is compatible with another plasmid pMM4 (Walton & Stewart 2002) carrying the Acinetobacter sp. cyclohexanone monooxygenase gene. The mutant strain, NADPH+ Lactone [BL21ΔgapA (pHL621, pMM4)], harbors two compatible plasmids pHL621 (carries the gapN gene) and pMM4 (carries the cyclohexanone monooxygenase gene). Expression was performed in shake flasks using the procedures outlined above. -caprolactone was produced as shown in TABLE 7.

TABLE 7

ε-CAPROLACTONE FORMATION IN NADPH+ CELLS.

| Strain | Rate (mM/hr) | Yield* (NADPH/glucose) |
|---|---|---|
| BL21(pDHC29, pMM4) | 2.49 ± 0.18 | 1.72 ± 0.19 |
| BL21ΔgapA(pHL621, pMM4) | 4.86 ± 0.16 | 2.97 ± 0.05 |

*calculated from ε-caprolactone formation

The mutant strain NADPH+ [BL21ΔgapA(pHL621, pMM4)] had a higher NADPH regeneration capability due to the presence of the NADP+-dependent GAPN (see FIG. 4A). NADPH+ cells had an higher NADPH/glucose yield than that of the control strain (2.97 vs. 1.72). In addition, the product formation rate of the mutant strain was also faster than that of the control strain (4.86 vs. 2.49). Thus increasing NADPH regeneration capability significantly improved process productivity (both yield and rate).

Plasmids expressing the BV monooxygenases are introduced into the engineered NADPH+ or NADPH++ E. coli and control strains. The strains are cultured and the NADPH, NADP, NADH, and NAD levels measured. Enzyme activity assays of the BV monooxygenase is taken from the cell samples. The product formed and glucose consumed is analyzed under non-growing conditions as described by Walton & Stewart (2002). The lactone is isolated and purified from cultures by adsorption and elution from an Amberlite XAD-4 resin. The isolated lactone is analyzed by gas chromatography. Non-chiral compounds are analyzed by GC-MS using a DB-17 column (0.25 mm×25 m, 0.25 micrometer film thickness) with flame ionization detection operating at 50° C. for 2 min, 50°-180° C. at 10/min, 180° C. 5 min. The injector temp is 225° C. and the detector is 250° C. Chiral isomers are separated with a CHIRASIL-DEX® CB column (0.25 mm×25 m, 0.25 micrometer film thickness) using helium carrier gas and flame ionization detection operated at 40° C. for 2 min, 400-120° at 1 degree per min, 120° C. for 5 min then 120°-180° C. at 5 degree/min then 180° C. for 15 min. The injector temp is 225° C. and the detector is 250° C. An internal standard of methyl benzoate is used. Analysis of the pathway flux by carbon-13 labeling is done in growing cells where an excess but non-inhibitory concentration of the cyclohexanone is present as substrate.

EXAMPLE 7

Lycopene Production

NADPH+ and NADPH++ strains previously described can host synthesis of lycopene by introducing E. herbicola's crtE, crtI and crtB genes from pACYC184 (CmR) (Cunningham et al., 1994). These model lycopene production strains have increased levels of NADPH availability. Lycopene levels are assayed using established protocols (Vadali et al., 2005).

Figure 4:
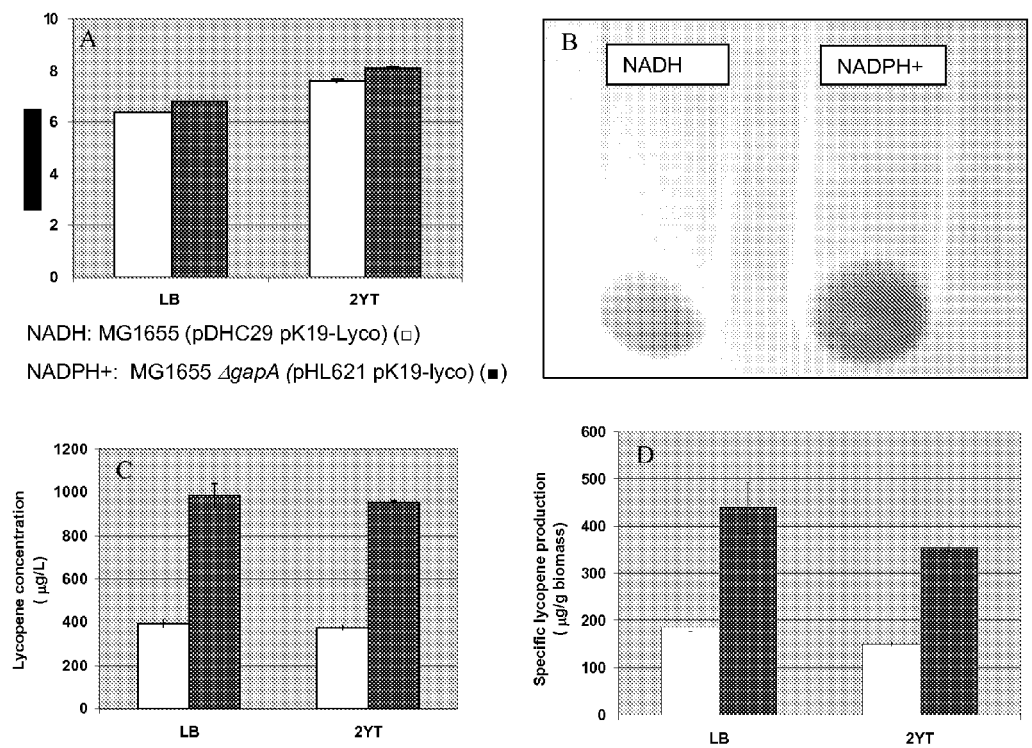
FIG. 4: Lycopene production in NADPH+ bacteria.
Figure 5:
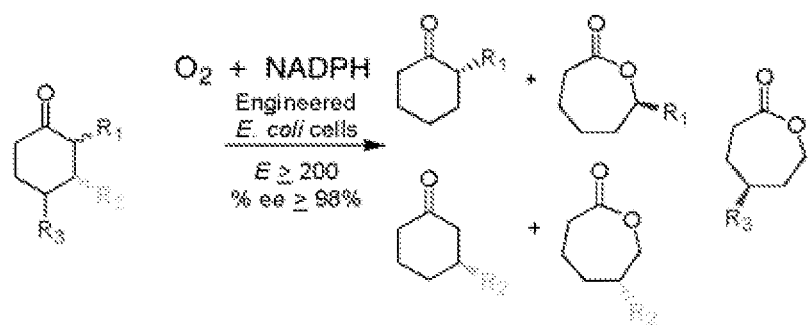
FIG. 5: BVMO catalyzed reactions on substituted cyclohexanones. Various chiral compounds are obtained depending on the substrate used. (Kyte et al., 2004).

In FIG. 4 lycopene was produced in NADH [MG1655 (pDHC29 pK19-Lyco)] and NADPH+ [MG1655 ΔgapA (pHL621 pK19-lyco)]. The dark red lycopene makes the cell pellet appear darker as shown in FIG. 4B. Increased cell viability (panel A) and increased lycopene production (panel C) led to a dramatic increase in lycopene per cell mass (panel D). Thus lycopene production was increased by increasing NADPH flux.

EXAMPLE 8

Metabolic Flux Analysis

The redistribution of intracellular metabolic fluxes upon cofactor perturbations are associated with NADP+/NADPH. Intracellular fluxes of the in vivo experiments are used to optimize NADPH levels and bioproduction in the engineered strains. The effect of concomitant chiral compound or lycopene production on metabolic flux distribution will determine ideal conditions for bioproduction of these compounds. Analysis of the pathway flux by carbon-13 labeling determines optimal pathway and carbon sources for compound bioproduction. By identifying carbon sources and rate limiting reactions, the bioproduction of PHAs, lycopene, lactones and other products can be optimized.

REFERENCES

All references are listed herein for the convenience of the reader. Each is incorporated by reference in its entirety.
1. Arkblad, et al., "*The cDNA sequence of proton-pumping nicotinamide nucleotide transhydrogenase from man and mouse*," Biochim Biophys Acta. 1273:203-5 (1996).
2. Arp, et al., "*Molecular and cellular fundamentals of aerobic cometabolism of trichloroethylene*," Biodegradation. 12:81-103 (2001).
3. Brzostowicz, et al., "*Identification of two gene clusters involved in cyclohexanone oxidation in Brevibacterium epidermidis strain HCU*," Appl. Microbiol. Biotechnol. 58:781-9 (2002).
4. Brzostowicz, et al., "*mRNA differential display in a microbial enrichment culture: simultaneous identification of three cyclohexanone monooxygenases from three species*," Appl. Environ. Microbiol. 69(1):334-42 (2003).
5. Choi, et al., "*A novel flavin-containing monooxygenase from Methylophaga sp strain SK1 and its indigo synthesis in Escherichia coli*," Biochem. Biophys. Res. Commun. 306(4):930-6 (2003).
6. Christensen and Nielsen, "*Isotopomer analysis using GC-MS*," Metab. Eng. 1:282-90 (1999).
7. Clarke, et al., "*Nucleotide sequence of the pntA and pntB genes encoding the pyridine nucleotide transhydrogenase of Escherichia coli*," Eur. J. Biochem. 158:647-53 (1986).
8. Cunningham, et al., (1994).
9. Datsenko and Wanner, "*One-step inactivation of chromosomal genes in Escherichia coli K-12 using PCR products*," Proc. Natl. Acad. Sci. U.S.A. 97:6640-5 (2000).
10. Fillinger, et al. "*Two glyceraldehyde-3-phosphate dehydrogenases with opposite physiological roles in a nonphotosynthetic bacterium*," J. Biol. Chem. 275:14031-7 (2000).
11. Fishman, et al., "*Controlling the regiospecific oxidation of aromatics via active site engineering of toluene para-monooxygenase of Ralstonia pickettii PKO1*," J. Biol. Chem. 280:506-14 (2005).
12. Fishman, et al., "*Protein engineering of toluene 4-monooxygenase of Pseudomonas mendocina KR1 for synthesizing 4-nitrocatechol from nitrobenzene*," Biotechnol Bioeng. 87:779-90 (2004).
13. Fitzpatrick, "*Mechanism of aromatic amino acid hydroxylation*," Biochemistry. 42:14083-91 (2003).
14. Fraaije, et al., "*Discovery of a thermostable Baeyer-Villiger monooxygenase by genome mining*," Appl. Microbiol. Biotechnol. 66(4):393-400 (2005).
15. Guyer, et al., "*Identification of a sex-factor-affinity site in E. coli as gamma delta*," Cold Spring Harbor Symp. Quant. Biol. 45:135-40 (1981).
16. Iwaki, et al., "*Cloning and characterization of a gene cluster involved in cyclopentanol metabolism in Comamonas sp. strain NCIMB 9872 and biotransformations effected by Escherichia coli-expressed cyclopentanone 1,2-monooxygenase*," Appl. Environ. Microbiol. 68(11): 5671-84 (2002) [Erratum in: Appl Environ Microbiol. 69(4):2414 (2003)]
17. Johanson, et al., "*Strain engineering for stereoselective bioreduction of dicarbonyl compounds by yeast reductases*," FEMS Yeast Res. 5:513-25 (2005).
18. Kamerbeek, et al., "*Substrate specificity and enantioselectivity of 4-hydroxyacetophenone monooxygenase*," Appl. Environ. Microbiol. 69:419-26 (2003).
19. Kamerbeek, et al., "*Identifying determinants of NADPH specificity in Baeyer-Villiger monooxygenases*," Eur. J. Biochem. 271:2107-16 (2004).
20. Kataoka, et al., "*Novel bioreduction system for the production of chiral alcohols*," Appl. Microbiol. Biotechnol. 62:437-445 (2003).
21. Kizaki, et al., "*Synthesis of optically pure ethyl (S)-4-chloro-3-hydroxybutanoate by Escherichia coli transformant cells coexpressing the carbonyl reductase and glucose dehydrogenase genes*," Appl. Microbiol. Biotechnol. 55(5):590-5 (2001).
22. Kyte, et al., "*Assessing the substrate selectivities and enantioselectivities of eight novel Baeyer-Villiger monooxygenases toward alkyl-substituted cyclohexanones*," J. Org. Chem. 69(1):12-7 (2004).
23. Lagenbach, et al., "*Functional expression of the PHA synthase gene phaC1 from Pseudomonas aeruginosa in Escherichia coli results in poly(3-hydroxyalkanoate) synthesis.*" FEMS Micorbiol. Lett. 150:303-9 (1997).
24. Leahy, et al., "*Evolution of the soluble diuron monooxygenases*," FEMS Microbiol. Rev. 27:449-79 (2003).
25. Lee, et al., "*Simultaneous biocatalyst production and Baeyer-Villiger oxidation for bioconversion of cyclohexanone by recombinant Escherichia coli expressing cyclohexanone monooxygenase*," Appl. Biochem. Biotechnol. 121-124:827-36 (2005).
26. Liu, et al., "*Asymmetric reduction of ethyl 4-chloro-3-oxobutanoate to ethyl (R)-4-chloro-3-hydroxybutanoate with two co-existing, recombinant Escherichia coli strains*," Biotechnol. Lett. 27(2):119-25 (2005).
27. Maicas S, et al., "*NAD(P)H regeneration is the key for heterolactic fermentation of hexoses in Oenococcus oeni.*" Microbiology. 148:325-32 (2002).
28. Malito, et al., "*Crystal structure of a Baeyer-Villiger monooxygenase*," Proc. Natl. Acad. Sci. USA. 101(36): 13157-62 (2004).
29. McClay, et al., "*Mutations of toluene-4-monooxygenase that alter regiospecificity of indole oxidation and lead to production of novel indigoid pigments*," Appl. Environ. Microbiol. 71:5476-83 (2005).
30. Mihovilovic, et al., "*Asymmetric Baeyer-Villiger oxidations of 4-mono-and 4,4-disubstituted cyclohexanones by whole cells of engineered Escherichia coli.*" J. Org. Chem. 66(3):733-8 (2001).
31. Mihovilovic, et al., "*First enantiodivergent Baeyer-Villiger oxidation by recombinant whole-cells expressing two monooxygenases from Brevibacterium*," Bioorg. Med. Chem. Lett. 13(8):1479-82 (2003).
32. Phillips, et al., "*High copy number plasmids compatible with commonly used cloning vectors*," Biotechniques. 28:400-6 (2000).
33. Qi, et al., "*Synthesis of poly(3-hydroxyalkanoates) in Escherichia coli expressing the PHA synthase gene phaC2 from Pseudomonas aeruginosa: comparison of PhaC1 and PhaC2*," FEMS Microbiol. Lett. 157:155-62 (1997).
34. Qi, et al., "*Metabolic routing towards polyhydroxyalkanoic acid synthesis acid synthesis in recombinant Escherichia coli (fadR): inhibition of fatty acid β-oxidation by acrylic acid.*" FEMS Microbil. Lett. 167:89-94 (1998).
35. Sheng, et al., "*Mechanistic studies of cyclohexanone monooxygenase: chemical properties of intermediates involved in catalysis*," Biochemistry 40(37): 11156-67 (2001).

36. Stafford, et al., "*Metabolic engineering of indene bioconversion in Rhodococcus sp.*," Adv. Biochem. Eng. Biotechnol. 73:85-101 (2001).
37. Stewart, "*Cyclohexanone Monooxygenase: A Useful Reagent for Asymmetric Baeyer-Villiger Reactions*," Curr. Org. Chem. 2:211-232 (1998).
38. Stewart, "*Organic transformations catalyzed by engineered yeast cells and related systems*," Curr. Opin. Biotechnol. 11(4):363-8 (2000).
39. Tao, et al., "*Altering toluene 4-monooxygenase by active-site engineering for the synthesis of 3-methoxycatechol, methoxyhydroquinone, and methylhydroquinone*," J. Bacteriol. 186:4705-13 (2004).
40. Van Beilen, et al., "*Cloning of Baeyer-Villiger monooxygenases from Comamonas, Xanthobacter and Rhodococcus using polymerase chain reaction with highly degenerate primers*," Environ. Microbiol. 5(3):174-82 (2003).
41. Vardar and Wood, "*Protein engineering of toluene-o-xylene monooxygenase from Pseudomonas stutzeri OX1 for enhanced chlorinated ethene degradation and o-xylene oxidation*," Appl. Microbiol. Biotechnol. 68:510-7 (2005).
42. Vardar, et al., "*Protein engineering of toluene-o-xylene monooxygenase from Pseudomonas stutzeri OX1 for oxidizing nitrobenzene to 3-nitrocatechol, 4-nitrocatechol, and nitrohydroquinone*," J. Biotechnol. 115:145-56 (2005).
43. Verho R, et al., "*Engineering redox cofactor regeneration for improved pentose fermentation in Saccharomyces cerevisiae.*" Appl Environ Microbiol. 69:5892-7 (2003).
44. Wackett, "*Directed evolution of new enzymes and pathways for environmental biocatalysis*," Ann. N. Y. Acad. Sci. 864:142-52 (1998).
45. Walton and Stewart, "*An efficient enzymatic Baeyer-Villiger oxidation by engineered Escherichia coli cells under non-growing conditions*," Biotechnol. Prog. 18(2):262-8 (2002).
46. Walton and Stewart, "*Understanding and improving NADPH-dependent reactions by nongrowing Escherichia coli cells*," Biotechnol. Prog. 20(2):403-11 (2004).
47. Weckbecker and Hummel, "*Improved synthesis of chiral alcohols with Escherichia coli cells co-expressing pyridine nucleotide transhydrogenase, NADP+-dependent alcohol dehydrogenase and NAD+-dependent formate dehydrogenase*," Biotechnol. Lett. 26:1739-44 (2004).
48. Willetts, "*Structural studies and synthetic applications of Baeyer-Villiger monooxygenases*," Trends Biotechnol. 15(2):55-62 (1997).
49. Williams et al., "*Cloning and sequencing of the genes for the proton-translocating nicotinamide nucleotide transhydrogenase from Rhodospirillum rubrum and the implications for the domain structure of the enzyme*," Microbiology 140:1595-604 (1996).
50. Zhu & Shimizu, "*Effect of a single-gene knockout on the metabolic regulation in Escherichia coli for D-lactate production under microaerobic condition*," Metab. Eng. 7:104-15 (2005).

The invention claimed is:

1. An engineered *Escherichia coli* comprising:
   a. a deleted gapA (ΔgapA) gene;
   b. an overexpressed DNA encoding gapC (an NADP-dependent D-glyceraldehyde-3-phosphate dehydrogenase (NADP-GAPDH)); and
   c. an overexpressed DNA encoding:
      i. a β-ketothiolase, an acetoacetyl-CoA reductase and a polyhydroxybutyric acid (PHB) synthase, wherein said cell produce 5-10 fold more PHB than a control cell lacking a) and b); or
      ii. a cyclohexanone monooxygenase, wherein said cell produces about 1.7 fold more caprolactone than a control cell lacking a) and b), or
      iii. a phytoene synthase, a geranylgeranyl pyrophosphate (GGDP) synthase, and phytoene desaturase, wherein said cell produces about 2.5 fold more lycopene than a control cell lacking a) and b).

2. The *Escherichia coli* of claim 1, wherein said DNA encoding said NADP-GAPDH is stably incorporated into a genomic insertion site in said cell.

3. The *Escherichia coli* of claim 1, said NADP-GAPDH having the amino acid sequence of SEQ ID NO. 1.

4. *Escherichia coli* of claim 2, said NADP-GAPDH having the amino acid sequence of SEQ ID NO. 1.

5. An engineered *Escherichia coli* comprising:
   a. a deleted gapA (ΔgapA) gene;
   b. an overexpressed DNA encoding gapC (an NADP-dependent D-glyceraldehyde-3-phosphate dehydrogenase (NADP-GAPDH)), wherein said gapC is the gene encoding the protein having amino acid sequence of SEQ ID NO. 1; and
   c. an overexpressed DNA encoding an NADPH utilizing enzyme, wherein said cell produces at least 1.7 fold more product from said NADPH utilizing enzyme than a control cell lacking a) and b).

* * * * *

```
SEQUENCE LISTING

<160> NUMBER OF SEQ ID NOS: 1

<210> SEQ ID NO 1
<211> LENGTH: 334
<212> TYPE: PRT
<213> ORGANISM: Clostridium acetobutylicum ATCC 824

<400> SEQUENCE: 1

Met Ala Lys Ile Ala Ile Asn Gly Phe Gly Arg Ile Gly Arg Leu Ala
1               5                   10                  15

Leu Arg Arg Ile Leu Glu Val Pro Gly Leu Glu Val Val Ala Ile Asn
            20                  25                  30

Asp Leu Thr Asp Ala Lys Met Leu Ala His Leu Phe Lys Tyr Asp Ser
        35                  40                  45

Ser Gln Gly Arg Phe Asn Gly Glu Ile Glu Val Lys Glu Gly Ala Phe
    50                  55                  60

Val Val Asn Gly Lys Glu Val Lys Val Phe Ala Glu Ala Asp Pro Glu
65                  70                  75                  80

Lys Leu Pro Trp Gly Asp Leu Gly Ile Asp Val Val Leu Glu Cys Thr
                85                  90                  95

Gly Phe Phe Thr Lys Lys Glu Lys Ala Glu Ala His Val Arg Ala Gly
            100                 105                 110

Ala Lys Lys Val Val Ile Ser Ala Pro Ala Gly Asn Asp Leu Lys Thr
        115                 120                 125

Ile Val Phe Asn Val Asn Asn Glu Asp Leu Asp Gly Thr Glu Thr Val
    130                 135                 140

Ile Ser Gly Ala Ser Cys Thr Thr Asn Cys Leu Ala Pro Met Ala Lys
145                 150                 155                 160

Val Leu Asn Asp Lys Phe Gly Ile Glu Lys Gly Phe Met Thr Thr Ile
                165                 170                 175
```

-continued

```
His Ala Phe Thr Asn Asp Gln Asn Thr Leu Asp Gly Pro His Arg Lys
            180                 185                 190

Gly Asp Leu Arg Arg Ala Arg Ala Ala Val Ser Ile Ile Pro Asn
        195                 200                 205

Ser Thr Gly Ala Ala Lys Ala Ile Ser Gln Val Ile Pro Asp Leu Ala
        210                 215                 220

Gly Lys Leu Asp Gly Asn Ala Gln Arg Val Pro Val Pro Thr Gly Ser
225                 230                 235                 240

Ile Thr Glu Leu Val Ser Val Leu Lys Lys Lys Val Thr Val Glu Glu
                245                 250                 255

Ile Asn Ala Ala Met Lys Glu Ala Ala Asp Glu Ser Phe Gly Tyr Thr
            260                 265                 270

Glu Asp Pro Ile Val Ser Ala Asp Val Val Gly Ile Asn Tyr Gly Ser
        275                 280                 285

Leu Phe Asp Ala Thr Leu Thr Lys Ile Val Asp Val Asn Gly Ser Gln
    290                 295                 300

Leu Val Lys Thr Ala Ala Trp Tyr Asp Asn Glu Met Ser Tyr Thr Ser
305                 310                 315                 320

Gln Leu Val Arg Thr Leu Ala Tyr Phe Ala Lys Ile Ala Lys
                325                 330
```